United States Patent
Orcutt et al.

(10) Patent No.: US 9,406,119 B2
(45) Date of Patent: Aug. 2, 2016

(54) ESTIMATING PHARMACOKINETIC PARAMETERS IN IMAGING

(75) Inventors: Kelly Davis Orcutt, Somerville, MA (US); John Hoppin, Boston, MA (US); Jacob Hesterman, Brighton, MA (US); Christian Lackas, Cologne (DE)

(73) Assignee: INVICRO, LLC, Boston, MA (US)

( * ) Notice: Subject to any disclaimer, the term of this patent is extended or adjusted under 35 U.S.C. 154(b) by 248 days.

(21) Appl. No.: 13/992,358

(22) PCT Filed: Dec. 8, 2011

(86) PCT No.: PCT/US2011/063954
§ 371 (c)(1),
(2), (4) Date: Nov. 22, 2013

(87) PCT Pub. No.: WO2012/078877
PCT Pub. Date: Jun. 14, 2012

(65) Prior Publication Data
US 2014/0321723 A1   Oct. 30, 2014

Related U.S. Application Data

(60) Provisional application No. 61/421,079, filed on Dec. 8, 2010.

(51) Int. Cl.
*G06K 9/00* (2006.01)
*G06T 7/00* (2006.01)
*G06F 19/00* (2011.01)

(52) U.S. Cl.
CPC ............ *G06T 7/0012* (2013.01); *G06F 19/704* (2013.01); *G06T 7/0016* (2013.01); *G06T 2207/10104* (2013.01); *G06T 2207/10108* (2013.01); *G06T 2207/30096* (2013.01); *G06T 2207/30104* (2013.01)

(58) Field of Classification Search
None
See application file for complete search history.

(56) References Cited

U.S. PATENT DOCUMENTS

| | | | |
|---|---|---|---|
| 7,693,320 B2 * | 4/2010 | Degani et al. | 382/131 |
| 8,194,963 B2 * | 6/2012 | Shinagawa et al. | 382/131 |
| 8,275,181 B2 * | 9/2012 | Muradyan et al. | 382/128 |
| 2004/0242994 A1 | 12/2004 | Brady et al. | |
| 2007/0165927 A1 * | 7/2007 | Muradyan et al. | 382/128 |
| 2009/0034814 A1 | 2/2009 | Shinagawa et al. | |

(Continued)

OTHER PUBLICATIONS

Miller et al., "Imaging angiogenesis: applications and potential for drug development", Journal of the National Cancer Institute, vol. 97, No. 3, Feb. 2, 2005.*

(Continued)

*Primary Examiner* — Soo Park
(74) *Attorney, Agent, or Firm* — Duane Morris LLP

(57) ABSTRACT

A method is provided for estimating a parameter of physiological significance. One or more images are provided of a tissue in a subject to whom a dose of a contrast agent (CA) has been administered, using a computer equipped with image processing software, the concentration or relative concentration of the agent in a region or regions of interest in the tissue is determined, thus generating concentration data. The time-based behavior of concentrations of CA within the tissue is determined using a pharmacokinetic model that is based on a set of pharmacokinetic model parameters. Using computer code, the pharmacokinetic model is fit to the concentration data, varying one or more parameters, such that a best fit estimate of a parameter of physiological significance is provided.

16 Claims, 7 Drawing Sheets

(56) References Cited

U.S. PATENT DOCUMENTS

2009/0185981 A1* 7/2009 Karczmar et al. ............. 424/9.3
2009/0190806 A1 7/2009 Muradyan
2009/0238428 A1 9/2009 Shinagawa et al.

OTHER PUBLICATIONS

Kellen and Bassingthwaighte, An integrative model of coupled water and solute exchange in the heart., Americal Journal of Physiology Heart and Circulatory Physiology 285(3):H1303-H1316, 2003.
Kellen and Bassingthwaighte, Transient transcapillary exchange of water driven by osmotic forces in the heart., Americal Journal of Physiology Heart and Circulatory Physiology 285(3):H1317-H1331, 2003.
Mescam et al., Multiscale model of liver DCE-MRI towards a better understanding of tumor complexity., IEEE Transactions on Medical Imaging. 29(3):699-707, 2010.
Anderson and Bassingthwaighte, Tracers in physiological systems modeling. In: Mathematical Modeling in Nutrition and Agriculture. Proceedings of 9th International Conference on Mathematical Modeling in Nutrition, Roanoke, VA, Aug. 14-17, 2006, edited by Mark D. Hanigan JN and Casey L Marsteller. Virginia Polytechnic Institute and State University, Blacksburg, VA, pp. 125-159, 2007.
Baxter and Jain, Pharmacokinetic analysis of the microscopic distribution of enzymeconjugated antibodies and prodrugs: comparison with experimental data, British Journal of Cancer 73:447-456, 1996.
Cheong et al., Dynamic contrast-enhanced CT of intracranial, eningioma: comparison of distributed and compartmental tracer kinetic models—initial results, Radiology 232:921-30, 2004.
Jackson et al., Mathematical and experimental analysis of localization of anti-tumour antibody-enzyme conjugates., British Journal of Cancer 80:1747-1753, 1999.
Krogh, The supply of oxygen to the tissues and the regulation of the capillary circulation, Journal of Physiology, 52:457-74, 1919.
Kuikka et al., Mathematical modelling in nuclear medicine., European Journal of Nuclear Medicine, 18:351-362, 1991.
Thurber and Weissleder, A systems approach for tumor pharmacokinetics, PLOS One, 6:e24696.
Thurber et al., Theoretic criteria for antibody penetration into solid tumors and micrometastases, Journal of Nuclear Medicine 48:995-999, 2007.
International Search Report (A3 38/2012), Sep. 9, 2012.
(IB/373) International Preliminary Report on Patentability Chapter I, Jun. 12, 2013.
Written Opinion of the International Search Authority Jun. 8, 2013.

* cited by examiner

ESTIMATING PHARMACOKINETIC PARAMETERS IN IMAGING

CROSS-REFERENCE TO RELATED APPLICATIONS

This application claims the benefit of the filing date of U.S. provisional application No. 61/421,079, which was filed Dec. 8, 2010, which is expressly incorporated by reference herein in its entirety.

FIELD OF THE INVENTION

The present invention relates to molecular imaging and mathematical modeling and more particularly to methods that use these techniques in concert to assess various physiological parameters relevant to drug development and patient treatment. For example, the present methods can be used to estimate tumor vascularity, contrast agent internalization rate, contrast agent binding affinity, and binding site concentration from molecular imaging data.

BACKGROUND

It is well known that studies are conducted in animals during preclinical drug development to determine in vivo pharmacokinetics, pharmacodynamics, efficacy, and toxicity, and that these studies are used in an effort to predict effective drug concentrations in humans. Advancements in small-animal imaging technology over the past decade have enabled quantitative assessment of dynamic in vivo distribution of radiolabeled compounds (Smith-Jones et al., Nature Biotechnol. 22:701-706, 2004; Robinson et al., Cancer Res. 65:1471-1478, 2005; Cai et al., Eur. J. Nucl. Med. Mol. Imaging 34:850-858, 2007; Cai et al., J. Nucl. Med. 48:304-310, 2007; Sosabowski et al., Star 40:2082-2089, 2009) as well as quantitative sub-organ analysis (Hoppin et al., J. Pharmacol. Exp. Ther. 337:350-358, 2011). Designing, performing, and interpreting these imaging studies is a complex, interdisciplinary effort. Many parameters define the results of an imaging study including isotope selection, radiolabeling chemistry, specific activity, injected activity, compound pharmacology, the animal model, imaging time points, imaging scan time, reconstruction algorithms, image processing, and others.

In the clinic, molecular imaging (primarily SPECT and PET) is a medical imaging technique in which a human subject can be imaged in two- or three-dimensions to quantitatively or semi-quantitatively determine the distribution of an administered exogenous contrast agent.

Existing approaches to analysis of PET and SPECT in the clinic include drawing regions of interest and determining the concentration or relative concentration of the contrast agent in the region of interest. However, it is unclear how the concentration of contrast agent is related to contrast agent and tumor properties.

SUMMARY

The present invention encompasses methods for estimating physiological parameters relevant to drug development and patient treatment from imaging data. The present methods can be used to estimate tumor and contrast agent properties from molecular imaging data, parameters which may be used in accelerating the development of cancer therapeutics, improving patient selection and stratification for clinical trials and treatment regimes, and monitoring patient responses to treatment. Thus, the featured methods can be used to improve not only the design and preclinical development of therapeutics, but also the clinical use of tumor targeting therapeutics and complementary biomarkers. More specifically, the methods allow in vivo molecular imaging to be used to quantitatively estimate physiological parameters such as antigen expression levels, contrast agent internalization rate, tumor vascularity, and contrast agent binding affinity. Furthermore, sub-organ quantitative analysis of tumors allows characterization of the variability of these tumor properties in vivo.

Parameters such as those mentioned above are often unknown or may be different in an in vivo versus an in vitro or ex vivo context. To estimate these parameters (and others) in vivo, we have developed a method to fit a pharmacokinetic model (varying one or more parameters) to experimental in vivo imaging data. Accordingly, the present invention features methods in which mathematical models are used in conjunction with imaging data to estimate parameters of physiological significance. Our methods use computer code to fit a model to imaging data. The best fit estimates a parameter or multiple parameters of physiological significance. Accordingly, the present invention is based, in part, on our development of methods that involve providing one or more images of a biological tissue that has been exposed to an imaging agent (e.g., the images can be obtained at set temporal intervals, which may be regular or irregular) and determining, using a computer equipped with image processing software, the concentration or relative concentration of the imaging agent in a region of interest in the tissue. A user then fits, using computer code, a pharmacokinetic model to the concentration data, varying one or more parameters so the best fit estimates a parameter or parameters of physiological significance. More specifically, in one embodiment, the average SUV (standardized uptake value) within the entire tumor ROI (region of interest (or multiple subsections of the tumor)) can be determined from imaging reconstruction, analysis, and quantification. The SUV-time data is then fit to the model varying antigen density and tumor vascularity (with known input parameters describing the ligand (affinity, specific activity, etc.) and the imaging study (time points, injected activity, body weight, arterial input function)). Similar methods can be used to determine antigen expression in normal tissues/organs.

In another aspect, the invention features a software system for performing the methods described above (e.g., for fitting a pharmacokinetic model to data).

One advantage of the present methods is their applicability to a variety of contexts. They can be used to predict the pharmacokinetics of tumor-targeted agents and to estimate select in vivo tumor parameters (binding affinity, antigen expression, vascularity, and internalization rate) from imaging data. The techniques are also applicable across species and translatable from the lab to the clinic. Accordingly, the subject can be any animal, including a rodent, dog, or non-human primate, useful in preclinical analysis. In other embodiments, the subject can be a human subject or patient. Further, our models provides several important capabilities: (1) the connection of in vitro/ex vivo characterization of new compounds and in vivo tumor imaging studies, (2) the estimation of tumor properties in vivo from molecular imaging data, and (3) characterization of free, bound, and internalized drug fractions in the tumor from imaging data.

DETAILED DESCRIPTION

The uptake of a given compound (e.g., a radiolabeled compound that can be imaged) by a tissue (e.g., a tumor) and the distribution of the compound in the tissue depends on a variety of parameters including, but not limited to, binding affinity, the concentration of binding sites within the tissue, and the extent to which the tissue is vascularized. PET, SPECT, MR and fluorescence imaging can be used to estimate the distribution of a compound (e.g., imaging agent) within a subject (e.g., a mammal such as a rodent, non-human primate or human). Image analysis techniques are applied to composite images in order to quantify the uptake or concentration of an imaging agent. For example, a radiologist can classify a tumor within a PET image and a region of interest can be created to segment said tumor within the image. The values of the image within the segmented tumor provide means of estimating the uptake and concentration of a pharmaceutical labeled with a positron emitter (e.g. $^{18}$F-fluorodeoxyglucose, the current market-leading PET radiopharmaceutical). An array of qualitative metrics for the distribution of radiopharmaceuticals are employed in nuclear medicine, most commonly some weighted form of the percent injected dose (% ID) such as the standardized uptake value (SUV) used extensively in PET imaging.

Estimating physiologically relevant tumor parameters in vivo is challenging. Tumor-targeted molecular imaging agents offer a great advance in this effort, though in practice their output is most often limited to uptake and concentration within the tumor at a fixed point in time. Imaging using multiple modalities (e.g. PET and MRI or PET and CT) often offers advanced anatomical information about tumors such as volume, morphology and in some cases vascularity. Combining this anatomical and functional imaging has been and continues to be a boon to oncologists, but is again limited in terms of characterizing more advanced physiology. Dynamic imaging of such agents offers significant improvements, often enabling the estimation of transport rates between plasma and tumor. The method put forward in this invention enables the estimation of a broader scope of understanding of tumor physiology; most notably the antigen density of the tumor, the internalization rate of the tumor-targeting compound and the vascularity of the tumor.

Figure 1:
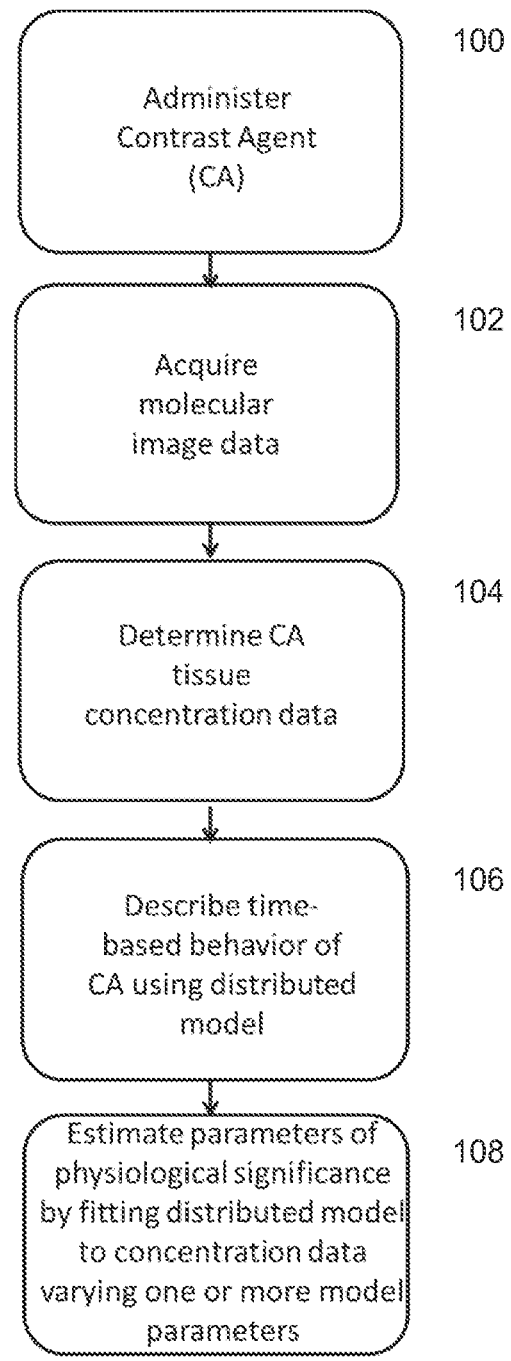
FIG. 1 is a flowchart illustrating a method for performing pharmacokinetic analysis in molecular imaging according to an exemplary embodiment of the present invention.

FIG. 1 illustrates a method for performing pharmacokinetic analysis in molecular imaging according to an exemplary embodiment described in detail below.

At step 100, a contrast agent is administered.

At step 102, molecular image data are acquired.

At step 104, CA tissue concentration data are determined.

At step 106, a model of the time-based behavior of the CA is described by the computer.

At step 108, parameters of physiological significance are determined by fitting the distributed model to the concentration data, varying one or more model parameters.

Specifically, we describe a method using a pharmacokinetic model of molecular transport in tumors and multiple time point SPECT or PET or MR or fluorescence imaging to quantitatively estimate an array of physiological parameters including the aforementioned number of binding sites in the tumor, the internalization rate of the imaging agent and the tumor vascularity to name a few. The methods put forward can include the steps of providing one or more images at set temporal intervals of a subject who has been exposed to an imaging agent; determining, using a computer equipped with image processing software, the concentration or relative concentration of the agent in a region of interest in the tissue, thereby generating concentration data; and fitting, using computer code, a pharmacokinetic model to the concentration data, varying one or more parameters such that the best fit estimates a parameter of physiological significance. In another embodiment, tumor vascularity can be measured by other means (e.g. MR or CT imaging) and in this case, only a single SPECT or PET or MR or fluorescence image may be necessary to quantitatively estimate a physiological parameter such as the number of binding sites in the tumor. In another embodiment, only a single SPECT or PET or MR or fluorescence image can be used to estimate a physiological parameter such as the number of binding sites in the tumor by providing the model with a limited range of other parameters such as tumor vascularity from the literature.

The pharmacokinetic model may be a distributed model. Distributed models, i.e. models that describe spatial as well as temporal variations (Cheong et al., *Radiology* 232:921-930, 2004; Mescam et al., *IEEE Trans. Med. Imaging*, 29:699-707, 2010; and Kellen and Bassingthwaighte, *Am. J. Physiol. Heart Circ. Physiol.* 285:H1303-1316, 2003) while more physiologically relevant (Anderson and Bassingthwaighte, Tracers in physiological systems modeling in Mathematical Modeling in Nutrition and Agriculture, Virginia Polytechnic Institute and State University, Roanoke, Va., 2006; Cheong, supra, and Kuikka et al., *Eur. J. Nucl. Med.* 18:351-362, 1991) have not yet been adopted widely by the preclinical and clinical research communities largely due to their mathematical complexity. For tumor targeting compounds, significant spatial heterogeneity is prevalent (Dennis et al., *Cancer Res.* 67:254-261, 2007; Primeau et al., *Clin. Cancer Res.* 11:8782-8788, 2005) and incorporating this spatial heterogeneity into mathematical models describing tumor uptake (and its validation with ex vivo assays such as immunohistochemistry) allows insight into drug microdistribution. In addition, the ability to tease out capillary permeability and tumor vascularity parameters from these models adds to the understanding of the effect of these parameters on in vivo distribution. For example, from the methods described here, one might predict antibody distribution in a tumor from imaging data of a radiolabeled peptide biomarker to improve patient selection in clinical trials. For example, one or more images may be provided at set temporal intervals of a subject who has been exposed to a HER2-specific contrast agent; determining, using a computer equipped with image processing software, the concentration or relative concentration of the agent in a tumor region of interest, thereby generating concentration data; and fitting, using computer code, a pharmacokinetic model to the concentration data, varying Bmax and vascularity parameters such that the best fit estimates tumor HER2 binding sites and tumor vascularity. These tumor parameters may then be used with the same pharmacokinetic model or a different one to predict the tumor uptake and macro- and/or micro-distribution of a HER2-targeting antibody (or other HER2-targeting protein or peptide) therapeutic. In this case, while tumor vascularity and HER2 expression would be assumed to remain the same, the tumor permeability of an antibody would be significantly different than that of the peptide due to molecular weight and thus the transport kinetics would be different. Using the tumor parameters estimated by the peptide, the transport and tumor targeting of the antibody can be predicted.

The distributed model may be based on Krogh cylinder geometry. The Krogh cylinder geometry was published in 1919 by August Krogh to describe oxygen transport in tissue (Krogh, *J. Physiol.* 52:409-415, 1919). In the past 20 years, the Krogh cylinder geometry has been used by several groups to describe molecular transport in tumors for both antibody and small molecule compounds (Jackson et al., *Br. J. Cancer,* 80:1747-1753, 1999; Baxter and Jain, *Br. J. Cancer,* 73:447-456, 1996; Thurber et al., *PLoS One,* 4:e8053, 2009; Thurber et al., *J. Nucl. Med.* 48:995-999, 2007). Distributed models based on the Krogh cylinder assume molecular transport by diffusion within the tumor interstitial space. These models have been validated in their ability to predict both average tumor uptake of antibodies (Jackson et al., supra, Baxter and Jain, supra) as well as antibody microdistribution in tumors (Thurber, 2007, supra).

An example of a distributed model based on the Krogh cylinder is described by the following partial differential equations and boundary and initial conditions:

$$\frac{\partial [C]}{\partial t} = D\nabla^2 [C] - \frac{k_{on}}{\varepsilon}[C][Ag] + k_{off}[B]$$

$$\frac{\partial [B]}{\partial t} = \frac{k_{on}}{\varepsilon}[C][Ag] - k_{off}[B] - k_{e,B}[B]$$

$$\frac{\partial [Ag]}{\partial t} = R_s - \frac{k_{on}}{\varepsilon}[C][Ag] + k_{off}[B] - k_{e,Ag}[Ag]$$

$$\frac{\partial [I]}{\partial t} = k_e[B] - k_{resid}[I]$$

$$\frac{\partial [C]}{\partial r}\bigg|_{r=R} = 0$$

$$-D\frac{\partial [C]}{\partial r}\bigg|_{r=Rcap} = P\left([C]_P - \frac{[C]}{\varepsilon}\right)$$

$$[C]|_{t=0} = 0$$

$$[B]|_{t=0} = 0$$

$$[Ag]|_{t=0} = Ag_0$$

$$[I]|_{t=0} = 0$$

wherein $\nabla^2$ denotes the Laplacian in cylindrical coordinates, [C] denotes the free CA concentration, [B] denotes the bound CA/antigen concentration, [Ag] denotes the unbound antigen concentration, [I] denotes the concentration of intracellular CA, D denotes the CA diffusion coefficient in tissue, $k_{on}$ denotes the CA/antigen association rate constant, $k_{off}$ denotes the CA/antigen dissociation rate constant, $\varepsilon$ denotes the CA void fraction in the tissue, $k_{e,B}$ denotes the internalization rate constant of the CA/antigen bound complex, $k_{e,Ag}$ denotes the internalization rate constant of the antigen, $k_{resid}$ denotes the rate of release of CA or CA signal from the intracellular compartment, $R_S$ denotes the antigen synthesis rate, R denotes the Krogh cylinder radius, $R_{cap}$ denotes the capillary radius, P denotes the tumor capillary permeability, $Ag_0$ denotes the initial antigen density, and $[C]_P$ denotes the plasma concentration of the contrast agent as a function of time, also sometimes called an arterial input function.

Capillary permeability (P), interstitial diffusivity (D), and void fraction ($\varepsilon$) can be measured experimentally (Thurber and Wittrup, *Cancer Res.* 68: 3334-3341, 2008, Yuan et al. *Cancer Res.* 55: 3752-3756, 1995). Capillary permeability (P), interstitial diffusivity (D), and void fraction ($\varepsilon$) can also be estimated from the molecular weight of the contrast agent based on empirical relationships derived in the literature (Schmidt and Wittrup, *Mol. Cancer Ther.* 8:2861-2871, 2009). $k_{on}$ can be measured experimentally or calculated from the dissociation constant ($K_D$) and $k_{off}$ ($k_{on}=k_{off}/K_D$), or assumed to be typical for antibodies and antibody fragments ($10^5$-$10^6 M^{-1}s^{-1}$). $k_{off}$ can be measured experimentally or calculated from $K_D$ and $k_{on}$ ($k_{off}=K_D\times k_{on}$). $k_{e,B}$ and $k_{e,Ag}$ can be measured experimentally (Schmidt et al. *Cancer Immunol Immunother.* 57:1879-1890, 2008) or varied within a physiological range. $k_{resid}$ depends on the isotope/fluorophore and labeling chemistry and can be measured experimentally (Press et al. *Cancer Res* 56: 2123-2129, 1996), or assumed to be equal to previous measurements reported in the literature for specific isotopes and labeling chemistry. $R_{cap}$ can be measured experimentally from biopsy sample(s) or assumed to be equal to previous measurements reported in the literature (Hilmas and Gillette. *Cancer* 33: 103-10, 1974). R can be measured experimentally from biopsy sample(s) or varied within a physiological range. $Ag_0$ can be measured experimentally from biopsy sample(s) or assumed to be varied within a physiological range. $Ag_0$ can also be estimated from $B_{max}$ (number of binding sites per cell) that can be measured experimentally and tumor cell density (number of tumor cells per volume of tumor): $Ag_0=B_{max}\times$cell density/Avogadro's number. $[C]_P$ can be measured experimentally from blood sample data or can be estimated from the image data. $R_S$ is calculated based on the input values $Ag_0$ and $k_{e,Ag}$ ($k_{e,Ag}\times Ag_0$).

The differential equations solve for C, B, I, and Ag, the concentration of free CA, bound CA, internalized CA, and free antigen, respectively, in the tumor as a function of time and distance from the capillary wall. For in vivo molecular imaging data, the total signal is a sum of the free, bound, and internalized contrast agent signal in the tumor tissue as well as the contrast agent signal in the tumor vascular space. From the total signal and the initial dose, specific activity, and tumor size, the average concentration, % ID/g, % ID, activity, SUV, and tumor to blood ratios can be calculated.

The model can be implemented in MATLAB using the method of lines with finite differences and an ordinary differential equation solver (such as ODE15s or ODE23. The model can be fit to image data using nonlinear optimization (such as with the Quasi-Newton or Nelder-Mead algorithms) to determine the parameter or parameters that result in the best fit of the model simulation to the image data.

Figure 5:
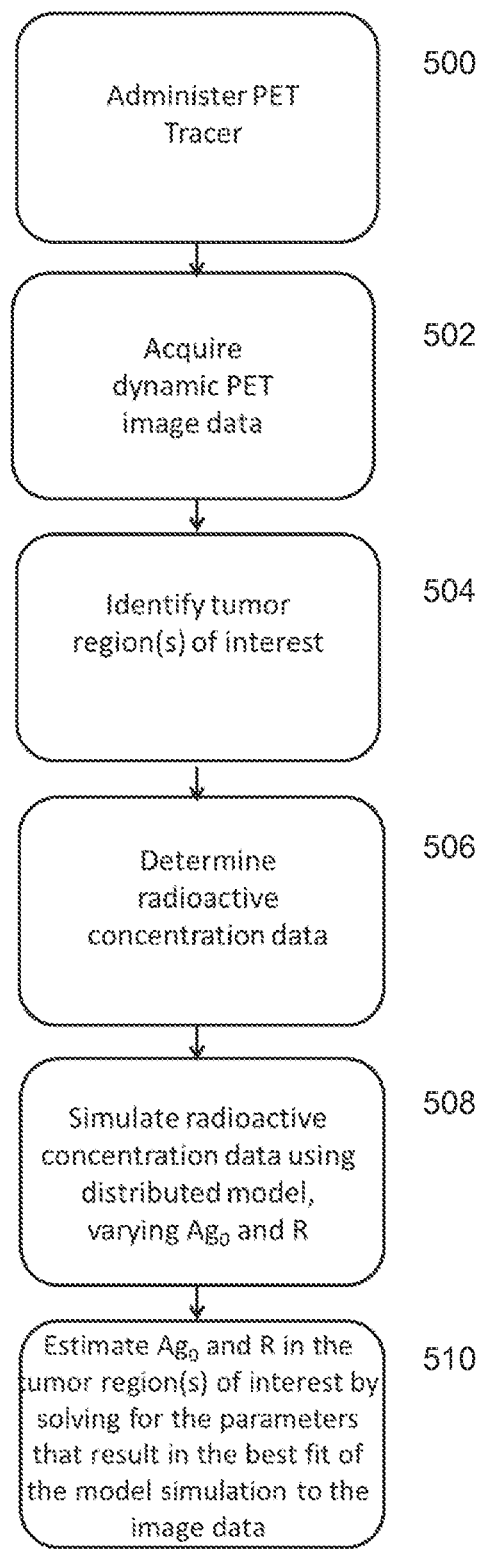
FIG. 5 is a flowchart illustrating a method for estimating antigen density ($Ag_0$) and capillary to capillary half-distance (R).

FIG. 5 is a flowchart summarizing a method for estimating antigen density ($Ag_0$) and capillary to capillary half-distance (R) using a PET tracer and resulting PET image data according to an exemplary embodiment of the present invention described in greater detail below.

At step 500, a PET tracer is administered.
At step 502, dynamic PET image data are acquired.
At step 504, a tumor region of interest is identified.
At step 506, radioactive concentration data are determined.
At step 508, the radioactive concentration data are simulated using a distributed model, varying $Ag_0$ and R.

At step 510, $Ag_0$ and R in the tumor region of interest are estimated by solving for the parameters that result in the best fit of the model simulation to the image data.

In one example (FIG. 5), $^{18}$F-galacto-RGD, a PET tracer that is $\alpha_v\beta_3$-selective is used as a contrast agent (Beer et al., *Clin Cancer Res.* 12:3942-3949, 2006). 4.5 mCi (2.4 nmol) of the contrast agent is administered to a subject who subsequently undergoes dynamic PET imaging at set time intervals. A radiologist may then classify a tumor within the PET images and a region of interest can be created to segment said tumor within the image. A computer equipped with image processing software is used to determine the concentration of the radioactivity in the classified tumor region of interest as a function of time. A Krogh cylinder distributed model may be used to simulate the concentration of the tracer as a function of time. For these simulations, the following parameters may be used (parameters are derived from in vitro, ex vivo, or in vivo assays): $k_{on}=10^5$ $M^{-1}s^{-1}$, $k_{off}=0.0008$ $s^{-1}$ ($K_D=k_{off}/k_{on}=8$ nM), $k_{e,B}=1.48\times10^{-5}$ $s^{-1}$, $k_{e,Ag}=1.48\times10^{-5}$ $s^{-1}$, $k_{resid}=1.6\times10^{-5}$ $s^{-1}$, $R_{cap}=8$ μm, D, P, and $\epsilon$ are estimated from the molecular weight of $^{18}$F-galacto-RGD (867 Da) using the relationships published in Schmidt and Wittrup, *Mol. Cancer Ther.* 8:2861-2871, 2009, $R_S=k_{e,Ag}\times Ag_0$, $[C]_P$ denotes plasma concentration of the compound as a function of time and is derived from subject blood samples. $[C]_P$ can also be estimated from image-derived arterial input functions or from previous patient averaged blood sample data. The parameters $Ag_0$ and R are varied for the simulations. The differential equations may be solved in MATLAB using the method of lines and the ODE solver ODE23s. The simulated total tumor concentration ($=[C]+[B]+[I]$) is converted from concentration units (nM) to % ID/g using the decay-corrected specific activity of the tracer and the total injected activity dose or to SUV using the total injected activity dose and body weight. The parameters $Ag_0$ and R are varied and a nonlinear optimization method such as a Nelder-Mead algorithm may be applied to solve for the parameters resulting in the best fit of the model to the image data. The parameters that result in the best fit estimate the concentration of $\alpha_v\beta_3$ binding sites in the tumor ($Ag_0$) and average capillary to capillary half-distance (R) in the classified tumor region of interest.

The contrast agents suitable for use in the present methods can be readily selected by one of ordinary skill in the art from those currently available and in current use as well as those developed at a later time. The currently available contrast agents include those that are commercially available. As noted, the contrast agent can be linked to a moiety (e.g., a peptide moiety) that binds a tumor antigen (i.e., a moiety expressed, and preferably selectively expressed, by a tumor cell). The moiety may mimic a therapeutic agent (by, for example, its ability to bind a tumor antigen) or it may be a therapeutic or potential therapeutic agent per se (including a small organic compound and a biotherapeutic, such as an antibody or other protein-based binding agent). For example, where the present methods are used to determine which of a plurality of potential therapeutic agents to advance from a pre-clinical to a clinical trial, one could label each of the potential therapeutic agents with a contrast agent and administer the labeled therapeutic agent to an animal model (e.g., a mouse having the type of tumor/cancer expected to be treated with the potential therapeutic agent). Following administration, and the procurement of images of the tumor, one would then subject those images to the methods described herein to determine which of the potential therapeutic agents performed best with respect to a parameter of physiological significance (e.g., tumor binding that is due, for example, to vascular permeability, high antigen expression and/or a high binding affinity).

Human tumor antigens are well studied in the art, and one can readily select an antigen of interest. For example, one could select a tumor antigen recognized by a T cell (as reviewed in Novellino et al. (*Cancer Immunol. Immunother.* 54:187-207, 2004) for targeting with a therapeutic or potential therapeutic agent. For example, researchers and clinicians working on breast cancer treatments could use a contrast agent linked to a moiety that targets an A1B1 coactivator protein, BRCA1, BRCA2, carbonic anhydrase, CD24, CEA, COX-2, creatine kinase, DAP kinase, endoglin (CD105), ErbB2, estrogen receptor beta, Ets1, EZH2, GCDFP-15, IGFBP-2, KAI-1 (CD82 or CD81/KAI-1, KLK15, MAGE-A, mammaglobin A, mammaglobin B, MCM2, MUC1 (CA15-3), a progesterone receptor, SRC-1 coactivator protein, STC-1, TEM-3, THRSP, and TIMP-1. Similarly, researchers and clinicians working on prostate cancer treatment could use a contrast agent linked to a moiety that targets PSA.

Once a potential therapeutic agent is selected for a clinical trial, one can continue to use the present methods to determine the agent's performance in humans suffering from a given cancer. Once launched as a therapeutic, the response of individual patients can be monitored to determine whether the therapeutic is having the desired effect or whether an alternate course should be prescribed. Accordingly, the present methods include those in which the analyses described herein are carried out before a patient begins treatment and during the course of treatment to determine efficacy.

Currently, immunohistochemistry (IHC) is the most commonly used test to assess tumor antigen expression levels. IHC test scores are used in treatment planning. For example, patients with HER2-positive scores (a score of 2+ to 3+ on a scale of 0 to 3+) tend to respond favorably to HER2-targeted therapies such as Herceptin. In one embodiment, image data is used to quantitatively assess tumor antigen expression level(s) in a subject and from this assessment, a patient may be selected to receive a targeted therapy based on the quantitative antigen expression level. For example, if the antigen expression level is estimated to be greater than a predetermined cut point then the patient would be selected to receive the therapy. An advantage to the method here compared to IHC is the ability to quantify tumor antigen expression levels in multiple tumors present in the body. For a patient with more than one tumor, the antigen expression level in each tumor may be quantified and the patient may be selected to receive targeted therapy if a predetermined metric, that is a function of the antigen expression estimates and the number of tumors, is greater than a predetermined cut point. In one embodiment, image data is used to quantitatively assess tumor antigen expression level(s) in a subject and from this assessment, a patient may be selected to be enrolled in a clinical trial based on the quantitative antigen expression level. For example, if the antigen expression level is estimated to be greater than a predetermined cut point then the patient would be enrolled in the trial. Similarly, for a patient with more than one tumor, the antigen expression level in each tumor may be quantified and the patient may be selected to receive targeted therapy if a predetermined metric, that is a function of the antigen expression estimates and the number of tumors, is greater than a predetermined cut point.

Further, this method enables the estimation of multiple numeric parameters of tumor physiology previously not available to oncologists. Numeric parameters derived from image data, e.g. cardiac ejection fraction, are in turn used to classify the disease state through a variety of decision strategies. In addition to estimating the existence and prevalence of tumor burden within a subject, estimating an array of parameters describing the numerical status of a tumor during the diagnostic stage and throughout therapy offers physicians and researchers means of measuring the efficacy of their therapy strategy.

Determining the optimal imaging protocol for a study is a complex problem. The ability to predict, even roughly, the pharmacokinetics for an imaging agent within the tumor offers considerable advantage when designing such a protocol.

Figure 6:
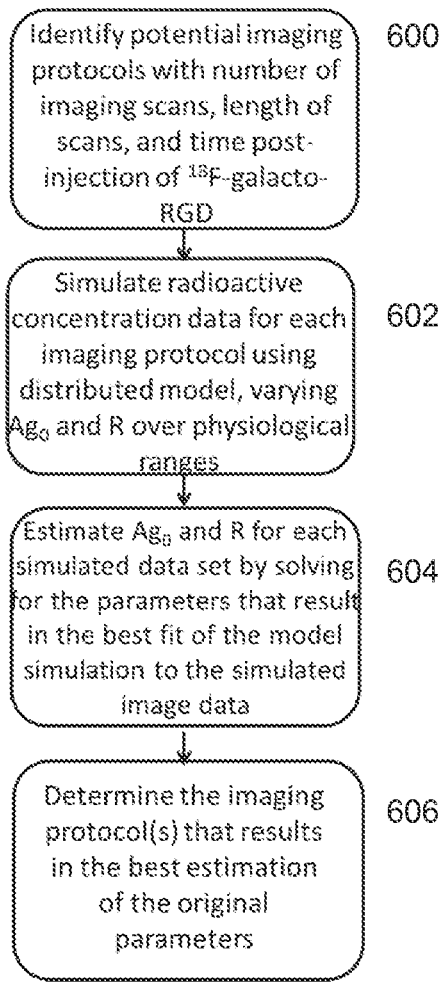
FIG. 6 is a flowchart illustrating a method for identifying an imaging protocol or protocols that result in best estimation of tumor parameters.

FIG. 6 is a flowchart illustrating a method for identifying an imaging protocol or protocols that result in best estimation of tumor parameters according to an exemplary embodiment of the present invention, described in detail below.

At step 600, potential imaging protocols are identified with a number of imaging scans, length of scans, and time post injection of $^{18}$F-galacto-RGD.

At step 602, radioactive concentration data are simulated for each imaging protocol using a distributed model, varying $Ag_0$ and R over physiological ranges.

At step 604, $Ag_0$ and R are estimated for each simulated data set by solving for the parameters that result in the best fit of the model simulation to the simulated image data.

At step 606, the programmed computer determines the imaging protocol that results in the best estimation of the original parameters.

In FIG. 6, an approach is presented using the methods here to determine the optimal imaging protocol for a given study based on a set or sets of model parameters. For example, the above parameters for $\alpha_\nu\beta_3$ may be used to generate simulations of tumor uptake as a function of time for varying $Ag_0$ and R over physiological ranges for different possible imaging protocols (i.e. number of image scans, and time and duration of imaging scans). Physiological ranges for $Ag_0$ and R may be 0-500 nM and 30-200 μm, respectively. Namely, one could for example select 10 values of $Ag_0$ and 10 values of R from the above ranges for a total of 100 combinations of $Ag_0$ and R. For each of these 100 pairs of $Ag_0$ and R one could generate a curve for the predicted uptake curve of the imaging agent within the tumor (a "time-activity curve") using the method and a computer. One could then have a set of parameters describing the imaging protocol, i.e., number of imaging scans, time post-injection of the imaging scans and the duration of the imaging scans. In general, these parameters are constrained by practical concerns. One could, however, determine 100 possible imaging protocols for example as defined by these three parameters: number of scans, time post-injection of scan and duration of scan. Given a predicted time-activity curve from the model and an imaging protocol, one can use the value on the predicted time-activity curve at each scheduled time in the protocol as the expected value for the uptake in the tumor in an experiment. One can, for example, use the scan duration at each time to determine the standard variation of the estimate of the uptake of the imaging agent in an experiment. Given an expected value and a standard deviation for the tumor uptake at each imaging time point in an experiment, one can use a computer to generate random samples for a given time-activity curve. In order to find the optimal imaging protocol, one can then run a simulation using a computer in which they generate many (e.g. 1000) simulated experiments for each of the possible imaging protocols. Given this simulated experimental data, one can estimate $Ag_0$ and R by fitting the model to the simulated tumor uptake date. One can compare the estimates of $Ag_0$ and R to the true values of $Ag_0$ and R used to simulate the experimental data using, for example, the square root of the mean-squared error between the true and estimated values. For each of the 100 possible combinations of $Ag_0$ and R, one can rank the 100 possible imaging protocols performance for estimating $Ag_0$ and R according to the average of the root-mean-squared error values. One can select the imaging protocol that provides the best estimates of $Ag_0$ and R across all 100 possible combinations of $Ag_0$ and R. The imaging protocol that provides the best estimate of $Ag_0$ and R can be defined as the optimal imaging protocol.

EXAMPLES

Example 1

Figure 2:
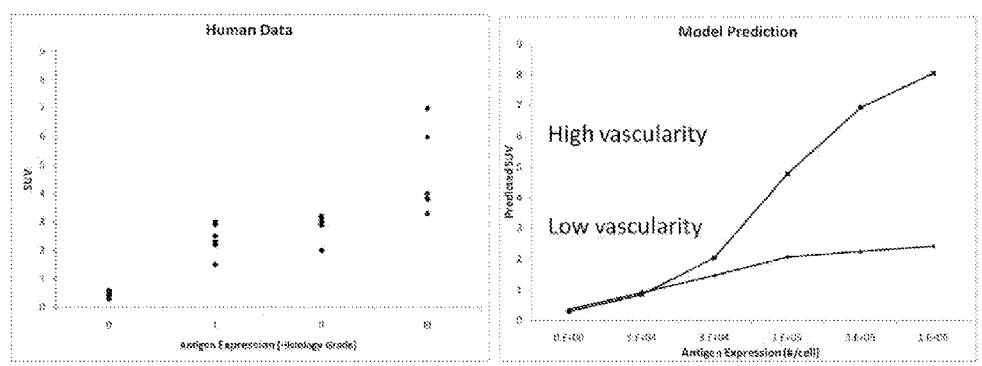
FIG. 2 shows diagrams of simulation data for integrin-binding $^{18}$F-galacto RGD in humans.

The Krogh cylinder geometry, on which our model is based, has been validated in the literature to predict both average tumor uptake of antibodies (Jackson et al., *Br. J. Cancer* 80:1747-1753, 1999; Baxter and Jain, *Br. J. Cancer* 73:447-456, 1996) as well as antibody microdistribution in tumors (Thurber et al., *J. Nucl. Med.* 48:995-999, 2007). We have compared model simulations to experimental data and have found that the model correlates very well with published experimental data for radiolabeled peptides and proteins. The model simulations were performed in MATLAB using the method of lines and the stiff ODE solver ode15s. Input parameters (e.g. binding affinity, blood clearance, internalization rate) were estimated from the literature. The sum of the radioactivity associated with free, bound, and internalized ligand was compared to the published total radioactivity in the tumor as assessed by ex vivo gamma counting. In addition to pre-clinical data, we have found that the model correlates well with clinical data. Beer et al. studied the correlation between SUV and integrin expression for $^{18}$F-galacto RGD in human tumors (*Clin. Cancer Res.* 12:394203949, 2006). We performed model simulations using parameters obtained from the literature. Simulations were compared to the reported PET imaging data and ex vivo immunohistochemistry (IHC) data (FIG. 2).

Model simulations were performed for integrin-binding $^{18}$F-galacto RGD in humans using parameters obtained from the literature: $k_{on}=10^5$ M$^{-1}$s$^{-1}$, $k_{off}=0.0008$ s$^{-1}$ ($K_D=k_{off}/k_{on}=8$ nM), $k_{e,B}=1.48\times10^{-5}$ s$^{-1}$, $k_{e,Ag}=1.48\times10^{-5}$ s$^{-1}$, $k_{resid}=1.6\times10^{-5}$ s$^{-1}$, $R_{cap}=8$ μm, D, P, and ε are estimated from the molecular weight of $^{18}$F-galacto-RGD (867 Da) using the relationships published in Schmidt and Wittrup, *Mol. Cancer Ther.* 8:2861-2871, 2009, $R_S=k_{e,Ag}\times Ag_0$, $[C]_P=C_0(Ae^{-\alpha t}+Be^{-\beta t})$, where $C_0$ is estimated from the injected dose (~2.4 nmol based on average literature reported specific activities of $^{18}$F-galacto-RGD) and the average plasma volume in a 70 kg person, 3.5 L, and A=0.82, α=2.6× 10$^{-3}$ s$^{-1}$, B=0.18, and β=1.4×10$^{-4}$ s$^{-1}$ were estimated from blood clearance curves of $^{18}$F-galacto-RGD in the literature. Two values of R were used, R=50 μm to represent a highly vascular tumor and R=100 μm to represent a weakly vascular tumor. The parameter $Ag_0$ was varied for the simulations. The differential equations were solved in MATLAB using the method of lines and the ODE solver ODE23s. The simulated total tumor concentration (=[C]+[B]+[I]) was converted from concentration units (nM) to SUV using the decay-corrected specific activity of the tracer to determine tumor activity concentration, the average injected dose (4.5 mCi) and a body weight of 70 kg. Simulation results (right plot) were compared to published clinical PET imaging data and ex vivo immunohistochemistry data (left plot)

The model accurately predicted the mean SUV (~0.4) at an average of 87 minutes post-injection for human tumors with no integrin expression (as determined by IHC). The model also accurately predicted the trend in increasing mean SUV for increasing integrin expression. The clinical PET data shows an increase in the variability of mean SUV with increasing integrin levels. The model captures this increase in variability when tumor vascularity is varied over typical values for human tumors. This analysis suggests that vascularity plays a role in SUV and that while there is certainly a correlation between antigen expression and SUV, SUV alone cannot be used to quantitatively estimate antigen expression in a tumor.

Example 2

Guanylyl cyclase C (GCC) is expressed on normal and malignant intestinal epithelial cells and is an attractive target for antibody-drug conjugate therapy. 5F9 has been identified as a picomolar-affinity antibody to GCC. We evaluate the dynamic in vivo distribution of $^{111}$In-labeled 5F9 antibody in xenograft mice bearing tumors with different levels of antigen expression using microSPECT/CT. A distributed model of molecular transport in tumors was used to estimate antigen density and tumor vascularity of GCC-expressing tumors in vivo. To investigate the accuracy of model estimations, vascular density was experimentally measured by vascular casting. Subcutaneous tumors were established in mice with a GCC-expressing cell line (GCC-293), a primary tumor line (PHTX-09C), and an antigen-negative cell line (HEK-293). ~500 μCi $^{111}$In-labeled 5F9 was injected into tumor-bearing mice (n=5). Mice were imaged by microSPECT/CT at 3, 24, 48, 96, and 144 hr post-injection. Vascular casting experiments were performed with microfil injections followed by CT imaging.

A nonlinear optimization tool using the Nelder-Mead algorithm was developed to fit a distributed model of molecular transport in tumors to in vivo imaging data to estimate tumor parameters in vivo. The distributed model was fit to the data varying average capillary to capillary half-distance (R) and antigen density ($Ag_0$=Bmax multiplied by average tumor cell density divided by Avogadro's number) over physiological ranges. Parameter maps of mean squared error (MSE) as a function of R and Bmax were generated for each fit (FIG. 3, MSE is represented in color with dark blue indicated lowest MSE and red indicating highest MSE).

Figure 3:
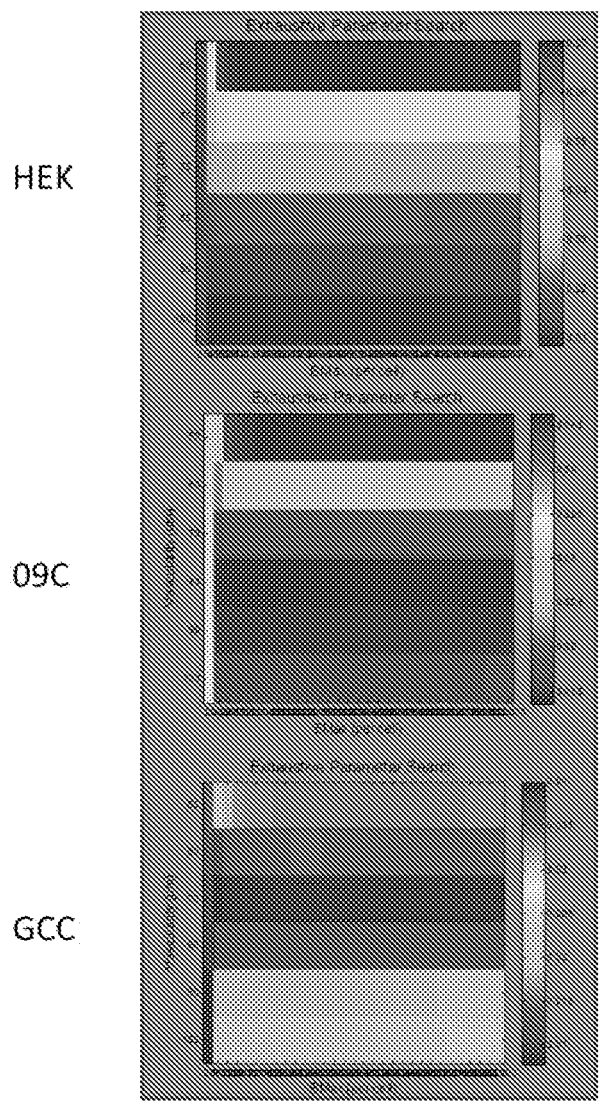
FIG. 3 depicts parameter maps for three tumor lines. Color bar represents MSE=mean squared error with better fit corresponding lower MSE values. Tumor vascularity as represented by the Krogh cylinder radius (R) was varied from 50 to 100 μm in 10 μm step sizes. Antigen density as represented by Bmax (number of antigen per cell) was varied from 0 to 600,000 #/cell in 20,000 #/cell step sizes.

In FIG. 3, Parameter maps for three tumor lines are shown. Color bar represents MSE=mean squared error with better fit corresponding lower MSE values. Tumor vascularity as represented by the Krogh cylinder radius (R) was varied from 50 to 100 um in 10 um step sizes. Antigen density as represented by Bmax (number of antigen per cell) was varied from 0 to 600,000 #/cell in 20,000 #/cell step sizes.

Figure 4:
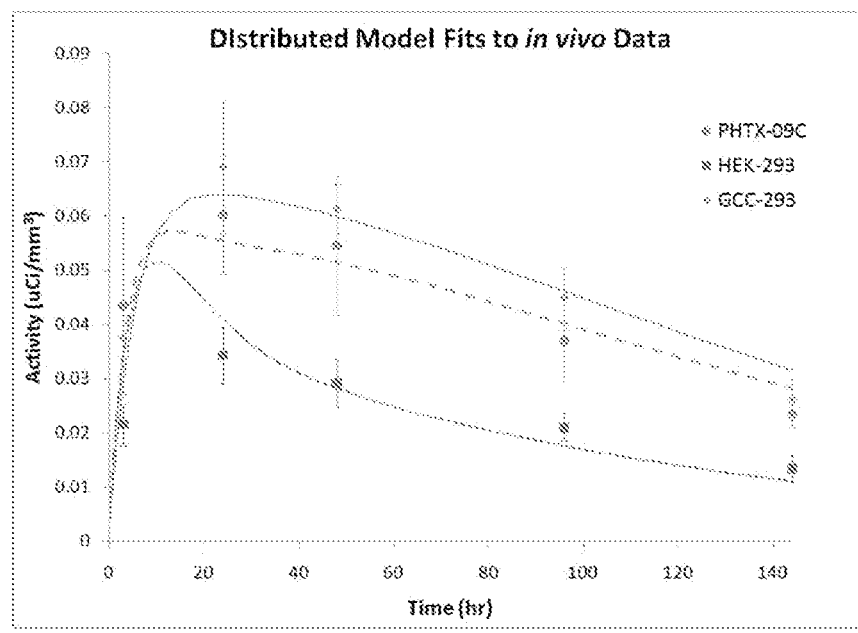
FIG. 4 shows best fit model simulations for three tumor lines, PHTX-09C, HEK-293, and GCC-293

The resulting best fit (i.e. lowest MSE) in vivo vascularity estimates were R=70 μm and 80 μm for the GCC-293 and PHTX-09C tumors, respectively and the best fit simulations of tumor uptake over time correlated very well with the experimental data (FIG. 4).

FIG. 4 shows best fit model simulations (solid and dotted lines) for three tumor lines, PHTX-09C, HEK-293, and GCC-293. Experimental data (average±standard deviation) is shown as triangles, circles, and squares, for GCC-293, PHTX-09C, and HEK-293, respectively, with error bars representing the standard deviation.

The estimated capillary to capillary half-distance correlated well with experimental measurements from vascular casting analysis. Because the model predicts the dose to be sub-saturating, only a lower limit to Bmax can be estimated from these experimental conditions (with MSE values not changing significantly for values above this limit). This lower limit was ~20,000 #/cell for 293-GCC and PHTX-09C tumors.

The methods and system described herein may be at least partially embodied in the form of computer-implemented processes and apparatus for practicing those processes. The disclosed methods may also be at least partially embodied in the form of tangible, non-transient machine readable storage media encoded with computer program code. The media may include, for example, RAMs, ROMs, CD-ROMs, DVD-ROMs, BD-ROMs, hard disk drives, flash memories, or any other non-transient machine-readable storage medium, wherein, when the computer program code is loaded into and executed by a computer, the computer becomes an apparatus for practicing the method. The media may include one or more local and/or remotely located media devices. The methods may also be at least partially embodied in the form of a computer into which computer program code is loaded and/or executed, such that the computer becomes a special purpose apparatus for practicing the methods. When implemented on a general-purpose processor, the computer program code segments configure the processor to create specific logic circuits. The methods may alternatively be at least partially embodied in a digital signal processor formed of application specific integrated circuits for performing the methods.

Figure 7:
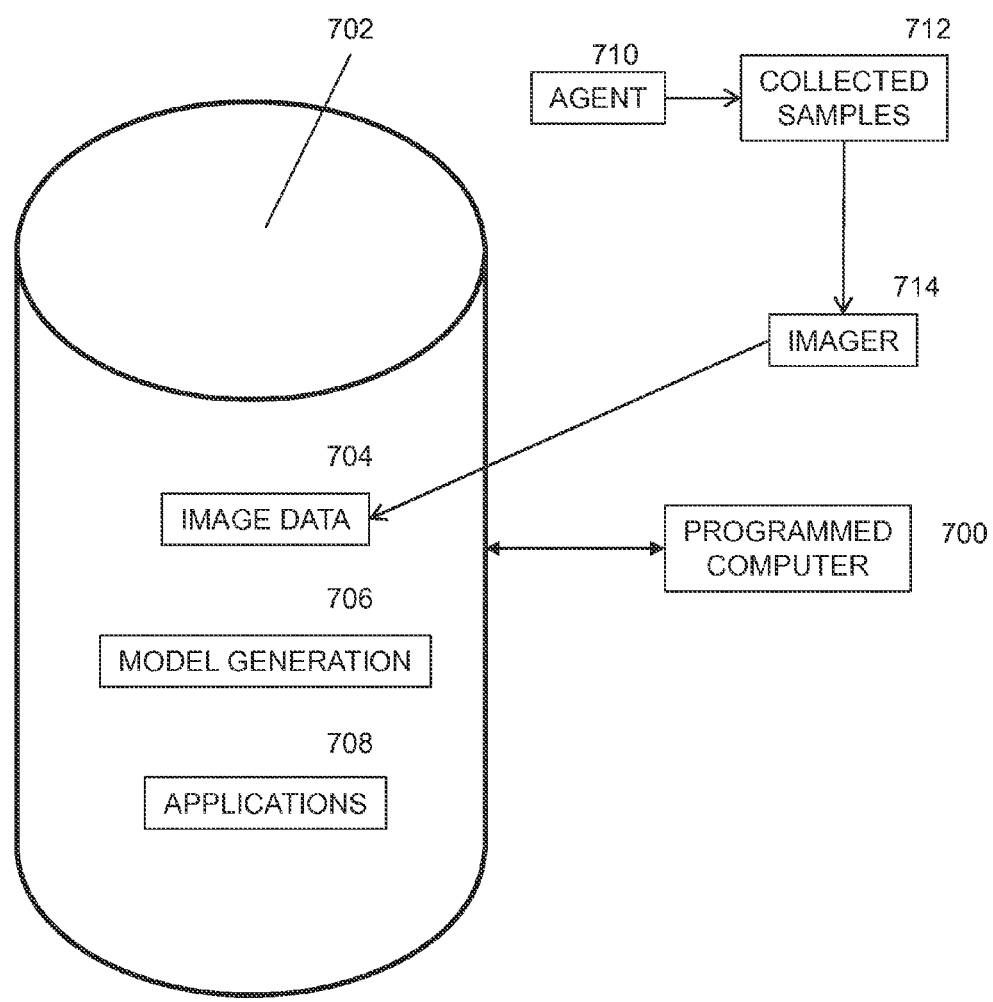
FIG. 7 is a block diagram of an exemplary programmed computer system for performing the method.

FIG. 7 is a block diagram of an apparatus for performing the method. A computer processor 700 is provided which may be a mainframe, microcomputer, embedded processor, or other processor system configured by programming to perform the computations and appropriate logical decisions described above. The processor 700 is capable of accessing one or more tangible, persistent computer readable storage medium(s) 702, which store image data 704, instructions and parameters 706 for generating the models described above, and optionally additional applications for further applying the concentration data to one or more particular problems, such as estimating $Ag_0$ and R in a tumor region of interest, selecting an imaging protocol, or the like. The image data 704 are collected by an electronic imager apparatus, such as any of the types mentioned above. The imager 714 collects the data from the samples 712 to which the CA 710 has been applied.

Although the subject matter has been described in terms of exemplary embodiments, it is not limited thereto. Rather, the appended claims should be construed broadly, to include other variants and embodiments, which may be made by those skilled in the art.

What is claimed is:
1. A method of estimating a parameter of physiological significance, the method comprising:
(a) providing one or more images of a tissue in a subject to whom a dose of a contrast agent (CA) has been administered; and
(b) determining, using a computer equipped with image processing software, the concentration or relative concentration of the agent in a region or regions of interest in the tissue, thereby generating concentration data;
(c) describing the time-based behavior of concentrations of CA within the tissue using a pharmacokinetic model that is based on a set of pharmacokinetic model parameters; and
(d) fitting, using computer code, the pharmacokinetic model to the concentration data, varying one or more parameters, wherein the best fit estimates a parameter of physiological significance, wherein the pharmacokinetic model for performing the analysis is a distributed model, and wherein the distributed model is based on the Krogh cylinder given by the following equations:

$$\frac{\partial [C]}{\partial t} = D\nabla^2 [C] - \frac{k_{on}}{\varepsilon}[C][Ag] + k_{off}[B]$$

$$\frac{\partial [B]}{\partial t} = \frac{k_{on}}{\varepsilon}[C][Ag] - k_{off}[B] - k_{e,B}[B]$$

$$\frac{\partial [Ag]}{\partial t} = R_s - \frac{k_{on}}{\varepsilon}[C][Ag] + k_{off}[B] - k_{e,Ag}[Ag]$$

$$\frac{\partial [I]}{\partial t} = k_e[B] - k_{resid}[I]$$

$$\left.\frac{\partial [C]}{\partial r}\right|_{r=R} = 0$$

$$-D\left.\frac{\partial [C]}{\partial r}\right|_{r=R_{cap}} = P\left([C]_p - \frac{[C]}{\varepsilon}\right)$$

$$[C]|_{t=0} = 0$$

$$[B]|_{t=0} = 0$$

$$[Ag]|_{t=0} = Ag_0$$

$$[I]|_{t=0} = 0$$

wherein $\nabla^2$ denotes the Laplacian in cylindrical coordinates, [C] denotes the free CA concentration, [B] denotes the bound CA/antigen concentration, [Ag] denotes the unbound antigen concentration, [I] denotes the concentration of intracellular CA, D denotes the CA diffusion coefficient in tissue, $k_{on}$ denotes the CA/antigen association rate constant, $k_{off}$ denotes the CA/antigen dissociation rate constant, $\varepsilon$ denotes the CA void fraction in the tissue, $k_{e,B}$ denotes the internalization rate constant of the CA/antigen bound complex, $k_{e,Ag}$ denotes the internalization rate constant of the antigen, $k_{resid}$ denotes the rate of release of CA or CA signal from the intracellular compartment, $R_S$ denotes the antigen synthesis rate, R denotes the Krogh cylinder radius, $R_{cap}$ denotes the capillary radius, P denotes the tumor capillary permeability, $Ag_0$ denotes the initial antigen density, and $[C]_P$ denotes the plasma concentration of the contrast agent as a function of time, also sometimes called an arterial input function.

2. The method of claim 1, wherein the contrast agent includes a positron- or gamma-emitting isotope.

3. The method of claim 2, wherein the positron- or gamma-emitting isotope is 68Ga, 18F, 89Zr, 64Cu, 86Y, 124I, 123I, 99mTc, 125I, 111In, 67Cu, or 177Lu.

4. The method of claim 1, wherein the contrast agent comprises paramagnetic or superparamagnetic material.

5. The method of claim 4, wherein the paramagnetic or superparamagnetic material is gadolinium, iron oxide, iron platinum, or manganese.

6. The method of claim 1, wherein the contrast agent comprises a fluorescent probe.

7. The method of claim 1, wherein the one or more images were generated by single photon emission computed tomography (SPECT), positron emission tomography (PET), magnetic resonance imaging (MRI), computed tomography (CT), detecting fluorescence, or a combination thereof.

8. The method of claim 1, wherein the parameter of physiological significance is the contrast agent affinity $K_D$, the Krogh cylinder radius R, the CA/antigen bound complex internalization rate $k_{e,B}$, and the antigen concentration $Ag_T$= [Ag]+[B], wherein $K_D$ represents the ratio of the dissociation rate $k_{off}$ to the association rate $k_{on}$ of contrast agent/antigen binding, R represents the capillary to capillary half-distance (a measure of tumor vascularity), $k_{e,B}$ represents the internalization rate of CA into the intracellular space, and $Ag_T$ represents the concentration of target antigen in the tumor.

9. A method of detecting a malignant lesion in a subject, the method comprising:
(a) providing one or more images of a subject to whom a dose of contrast agent (CA) has been administered;
(b) identifying a lesion candidate based on the acquired image or images;
(c) determining, using a computer equipped with image processing software, the concentration or relative concentration of the CA in a region of interest in the tissue, thereby generating concentration data;
(d) describing the time-based behavior of concentrations of the CA within the subject using a pharmacokinetic model that is based on a set of pharmacokinetic model parameters;
(e) fitting, using computer code, the pharmacokinetic model to the concentration data, varying one or more parameters wherein the best fit estimates a parameter or parameters of physiological significance; and
(f) determining whether the lesion candidate is a malignant lesion based on the concentration data and the estimated parameter or parameters of physiological significance,
wherein the pharmacokinetic model for performing the analysis is a distributed model that describes spatial and temporal variations, and wherein the distributed model is based on the Krogh cylinder given by the following equations:

$$\frac{\partial [C]}{\partial t} = D\nabla^2 [C] - \frac{k_{on}}{\varepsilon}[C][Ag] + k_{off}[B]$$

$$\frac{\partial [B]}{\partial t} = \frac{k_{on}}{\varepsilon}[C][Ag] - k_{off}[B] - k_{e,B}[B]$$

$$\frac{\partial [Ag]}{\partial t} = R_s - \frac{k_{on}}{\varepsilon}[C][Ag] + k_{off}[B] - k_{e,Ag}[Ag]$$

$$\frac{\partial [I]}{\partial t} = k_e[B] - k_{resid}[I]$$

$$\left.\frac{\partial [C]}{\partial r}\right|_{r=R} = 0$$

$$-D\left.\frac{\partial [C]}{\partial r}\right|_{r=R_{cap}} = P\left([C]_p - \frac{[C]}{\varepsilon}\right)$$

$$[C]|_{t=0} = 0$$

$$[B]|_{t=0} = 0$$

$$[Ag]|_{t=0} = Ag_0$$

$$[I]|_{t=0} = 0$$

wherein $\nabla^2$ denotes the Laplacian in cylindrical coordinates, [C] denotes the free CA concentration, [B] denotes the bound CA/antigen concentration, [Ag] denotes the unbound antigen concentration, [I] denotes the concentration of intracellular CA, D denotes the CA diffusion coefficient in tissue, $k_{on}$ denotes the CA/antigen association rate constant, $k_{off}$ denotes the CA/antigen dissociation rate constant, $\varepsilon$ denotes the CA void fraction in the tissue, $k_{e,B}$ denotes the internalization rate constant of the CA/antigen bound complex, $k_{e,Ag}$ denotes the internalization rate constant of the antigen, $k_{resid}$ denotes the rate of release of CA or CA signal from the intracellular compartment, $R_S$ denotes the antigen synthesis rate, R denotes the Krogh cylinder radius, $R_{cap}$ denotes the capillary radius, P denotes the tumor capillary permeability, $Ag_0$ denotes the initial antigen density, and $[C]_P$ denotes the plasma concentration of the contrast agent as a function of time, also sometimes called an arterial input function.

10. A method of detecting a malignant lesion in a subject, the method comprising:
    (a) providing one or more images of a subject to whom a dose of contrast agent (CA) has been administered;
    (b) identifying a lesion candidate based on the acquired image or images;
    (c) determining, using a computer equipped with image processing software, the concentration or relative concentration of the CA in a region of interest in the tissue, thereby generating concentration data;
    (d) describing the time-based behavior of concentrations of the CA within the subject using a pharmacokinetic model that is based on a set of pharmacokinetic model parameters;
    (e) fitting, using computer code, the pharmacokinetic model to the concentration data, varying one or more parameters wherein the best fit estimates a parameter or parameters of physiological significance; and
    (f) determining whether the lesion candidate is a malignant lesion based on the concentration data and the estimated parameter or parameters of physiological significance,
    wherein the pharmacokinetic model for performing the analysis is a distributed model that describes spatial and temporal variations, and, where the parameter of physiological significance is the contrast agent affinity $K_D$, the Krogh cylinder radius R, the CA/antigen bound complex internalization rate $k_{e,B}$, and the antigen concentration $Ag_T=[Ag]+[B]$, wherein $K_D$ represents the ratio of the dissociation rate $k_{off}$ to the association rate $k_{on}$ of contrast agent/antigen binding, R represents the capillary to capillary half-distance, which is a measure of tumor vascularity, $k_{e,B}$ represents the internalization rate of CA into the intracellular space, and $Ag_T$ represents the concentration of target antigen in the tumor.

11. The method of claim 10, wherein the contrast agent includes a positron- or gamma-emitting isotope.

12. The method of claim 10, wherein the contrast agent comprises paramagnetic or superparamagnetic material.

13. The method of claim 10, wherein the contrast agent comprises a fluorescent probe.

14. The method of claim 10, wherein the one or more images were generated by single photon emission computed tomography (SPECT), positron emission tomography (PET), magnetic resonance imaging (MRI), computed tomography (CT), detecting fluorescence, or a combination thereof.

15. A computer system comprising: a processor; and a program storage device readable by the computer system, embodying a program instructions executable by the processor to perform method steps for performing pharmacokinetic analysis in image(s), the method comprising:
    (a) providing one or more images of a subject to whom a contrast agent (CA) has been administered;
    (b) identifying a lesion candidate based on the one or more images;
    (c) determining, using a computer equipped with image processing software, the concentration or relative concentration of the CA in a region of interest in the tissue, thereby generating concentration data;
    (d) describing the time-based behavior of concentrations of CA within the subject using a pharmacokinetic model that is based on a set of pharmacokinetic model parameters; and
    (e) fitting, using computer code, the pharmacokinetic model to the concentration data, varying one or more parameters, wherein the best fit estimates a parameter or parameters of physiological significance,
    wherein the pharmacokinetic model for performing pharmacokinetic analysis is a distributed model, wherein the distributed model is based on the Krogh cylinder given by the following equations:

$$\frac{\partial [C]}{\partial t} = D\nabla^2 [C] - \frac{k_{on}}{\varepsilon}[C][Ag] + k_{off}[B]$$

$$\frac{\partial [B]}{\partial t} = \frac{k_{on}}{\varepsilon}[C][Ag] - k_{off}[B] - k_{e,B}[B]$$

$$\frac{\partial [Ag]}{\partial t} = R_S - \frac{k_{on}}{\varepsilon}[C][Ag] + k_{off}[B] - k_{e,Ag}[Ag]$$

$$\frac{\partial [I]}{\partial t} = k_e[B] - k_{resid}[I]$$

$$\left.\frac{\partial [C]}{\partial r}\right|_{r=R} = 0$$

$$-D\left.\frac{\partial [C]}{\partial r}\right|_{r=R_{cap}} = P\left([C]_P - \frac{[C]}{\varepsilon}\right)$$

$$[C]|_{t=0} = 0$$

$$[B]|_{t=0} = 0$$

$$[Ag]|_{t=0} = Ag_0$$

$$[I]|_{t=0} = 0$$

wherein $\nabla^2$ denotes the Laplacian in cylindrical coordinates, [C] denotes the free CA concentration, [B] denotes the bound CA/antigen concentration, [Ag] denotes the unbound antigen concentration, [I] denotes the concentration of intracellular CA, D denotes the CA diffusion coefficient in tissue, $k_{on}$ denotes the CA/antigen association rate constant, $k_{off}$ denotes the CA/antigen dissociation rate constant, $\varepsilon$ denotes the CA void fraction in the tissue, $k_{e,B}$ denotes the internalization rate constant of the CA/antigen bound complex, $k_{e,Ag}$ denotes the internalization rate constant of the antigen, $k_{resid}$ denotes the rate of release of CA or CA signal from the intracellular compartment, $R_S$ denotes the antigen synthesis rate, R denotes the Krogh cylinder radius, $R_{cap}$ denotes the capillary radius, P denotes the tumor capillary permeability, $Ag_0$ denotes the initial antigen density, and $[C]_P$ denotes the plasma concentration of the contrast agent as a function of time, also sometimes called an arterial input function.

16. The computer system of claim 15, wherein the one or more parameters of physiological significance are the contrast agent affinity $K_D$, the Krogh cylinder radius R, the CA/antigen bound complex internalization rate $k_{e,B}$, and the antigen concentration $Ag_T=[Ag]+[B]$, wherein $K_D$ represents the ratio of the dissociation rate $k_{off}$ to the association rate $k_{on}$ of contrast agent/antigen binding, R represents the capillary to capillary half-distance, which is a measure of tumor vascularity, $k_{e,B}$ represents the internalization rate of CA into the intracellular space, and $Ag_T$ represents the concentration of target antigen in the tumor.

* * * * *